US00PP28957P2

(12) United States Plant Patent
Boer

(10) Patent No.: US PP28,957 P2
(45) Date of Patent: Feb. 13, 2018

(54) ***SAMBUCUS* PLANT NAMED 'JDEBOER001'**

(50) Latin Name: *Sambucus nigra*
Varietal Denomination: Jdeboer001

(71) Applicant: Jan de Boer, Boelenslaan (NL)

(72) Inventor: Jan de Boer, Boelenslaan (NL)

( * ) Notice: Subject to any disclaimer, the term of this patent is extended or adjusted under 35 U.S.C. 154(b) by 31 days.

(21) Appl. No.: 14/999,729

(22) Filed: Jun. 20, 2016

(51) Int. Cl.
*A01H 5/02* (2006.01)

(52) U.S. Cl.
USPC ..... Plt./226

(58) Field of Classification Search
None
See application file for complete search history.

(56) References Cited

PUBLICATIONS

UPOV hit on *Sambucus* plant named 'Jdeboer001', QZ PBR 20142240, filed Sep. 17, 2014.*

* cited by examiner

*Primary Examiner* — Anne M Grunberg
(74) *Attorney, Agent, or Firm* — Penny J Aguirre

(57) ABSTRACT

A new cultivar of *Sambucus* plant named 'Jdeboer001' that is characterized by its an upright and spreading plant habit, its deeply dissected foliage that is yellow-green in color orbicular shaped plant habit and its leaves that are ovate in shape.

2 Drawing Sheets

Genus/species: *Sambucus nigra.*
Varietal denomination: 'Jdeboer001'.

CROSS REFERENCE TO A RELATED APPLICATION

This application is related to a European plant breeders' rights application filed on Sep. 17, 2014, application No. 2014-2240. There have been no offers for sale anywhere in the world prior to the filing of this Application and no accessibility to one of ordinary skill in the art could have been derived from the printed plant breeder's rights documents.

BACKGROUND OF THE INVENTION

The present invention relates to a new and distinct cultivar of *Sambucus nigra* and will be referred to hereafter by its cultivar name, 'Jdeboer001'. 'Jdeboer001' represents a new cultivar of Elderberry, a deciduous shrub grown for landscape use.

'Jdeboer001' was discovered by the Inventor in the May of 2000 as a chance seedling growing in his trial plot in Feanwalden, The Netherlands. The new cultivar was found growing among several different unnamed cultivars of *Sambucus*, the exact parentage is therefore unknown.

Asexual propagation of the new cultivar was first accomplished by the Inventor by softwood stem cuttings in summer of 2000 in Feanwalden, The Netherlands. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new *Sambucus*. These attributes in combination distinguish 'Jdeboer001' as a unique cultivar of *Sambucus.*

1. 'Jdeboer001' exhibits an upright and spreading plant habit.
2. 'Jdeboer001' exhibits deeply dissected foliage that is yellow-green in color.
3. 'Jdeboer001' exhibits leaves that are ovate in shape.

'Jdeboer001' can be most closely compared to the *Sambucus* cultivars 'Walfinb' (U.S Plant Pat. No. 26,425) and 'SMNSRD4' (U.S. Plant Pat. No. 26,613). 'Walfinb' differs from 'Jdeboer001' in having leaves that are longer and more elliptical in shape, and in having new foliage that is brighter gold in color. 'SMNSRD4' differs from 'Jdeboer001' in having leaves that are oblanceolate to lanceolate in shape, and in having a more mounded plant habit.

BRIEF DESCRIPTION OF THE DRAWINGS

The accompanying colored photographs illustrate the overall appearance and distinct characteristics of the new *Sambucus*. The photographs were taken of a 2 year-old plant as grown outdoors in a 19-cm container in Feanwalden, The Netherlands.

The photograph in FIG. 1 provides a side view of the plant habit of 'Jdeboer001'.

Figure 1:
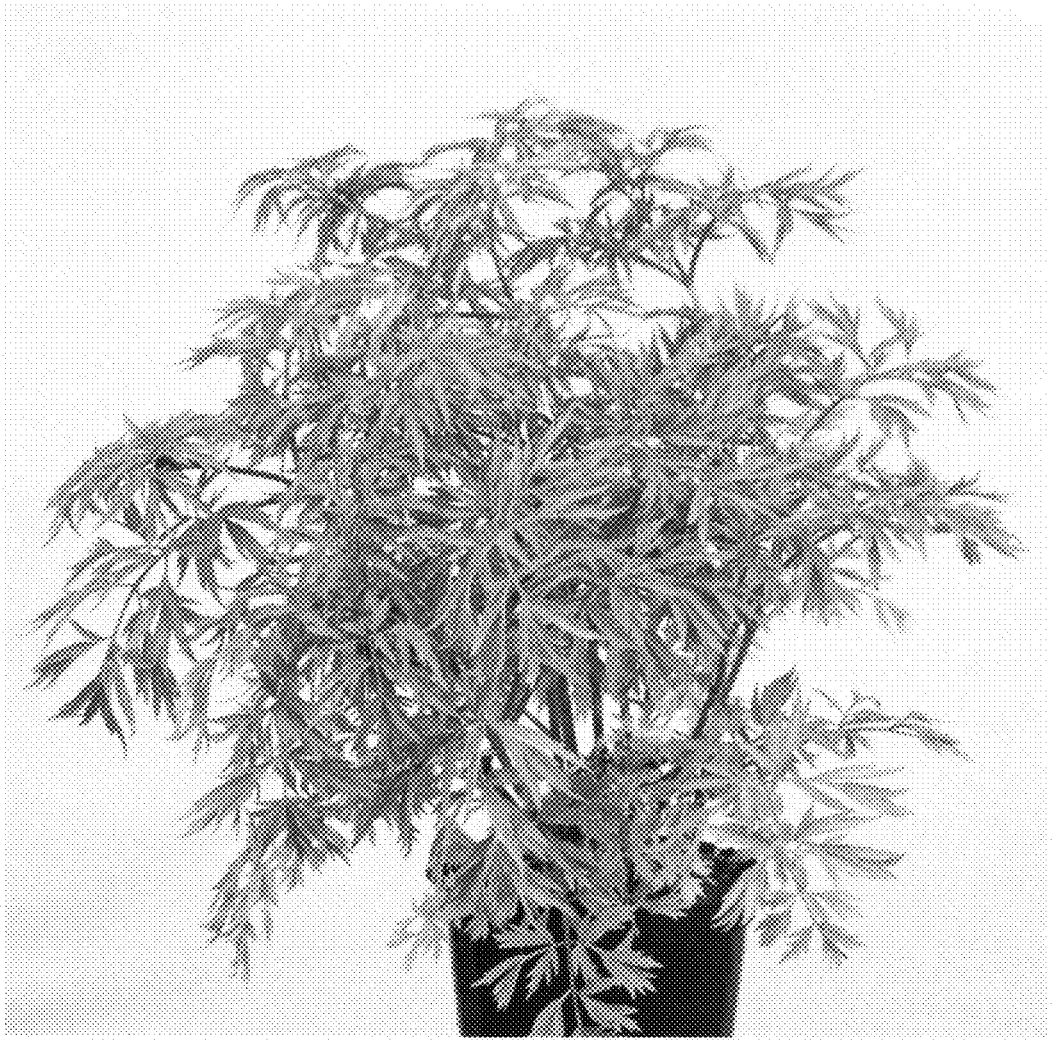
Figure 2:
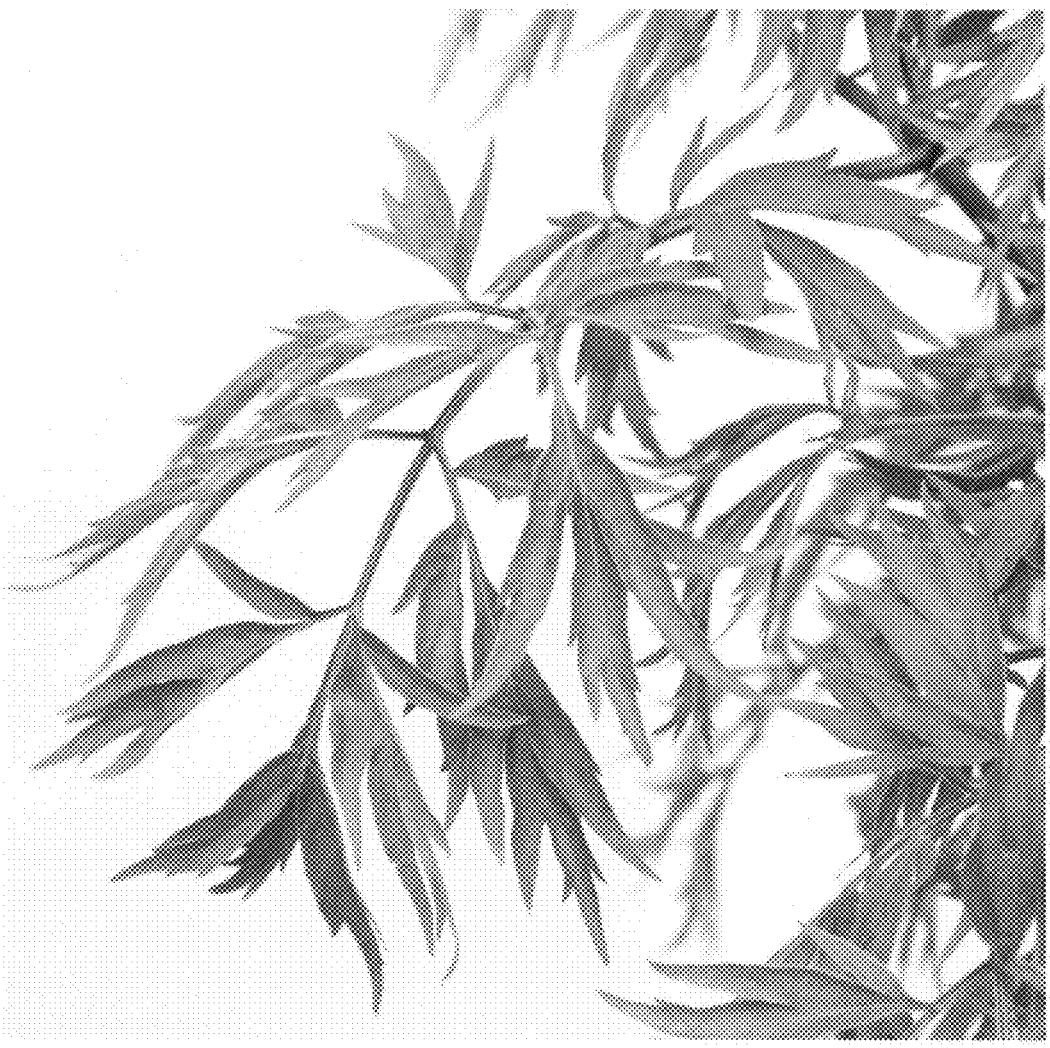

The photograph in FIG. 2 provides a close-up view of the foliage of 'Jdeboer001'.

The colors in the photographs are as close as possible with the photographic and printing technology utilized and the color values cited in the detailed botanical description accurately describe the colors of the new *Sambucus.*

BOTANICAL DESCRIPTION OF THE PLANT

The following is a detailed description of 2 year-old plants of the new cultivar as grown outdoors in 19-cm containers in Feanwalden, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Plant type.*—Deciduous shrub.

*Plant habit*—Upright, orbicular form.

*Height and spread.*—An average of 45 cm in height and 52 cm in diameter as grown in a 19-cm container.

*Hardiness.*—At least in U.S.D.A. Zones 5 to 9.

*Diseases and pest resistance.*—No susceptibility or resistance to diseases or pests has been observed.

*Root description.*—Fibrous and fine, 165C in color.

*Growth rate.*—Moderately vigorous.

*Propagation.*—Softwood stem cuttings.

*Root development.*—About 3 weeks to initiate roots and 2 months to produce a young plant.

Branch description:

*Branch color.*—Young; 144A, mature and bark; 199D, internode color; 200C to 200D.

*Branch size.*—Up to 31.9 m in length and 5 mm in diameter.

*Stem shape.*—Rounded, moderately angulate with an average of 6 angles.

*Stem quantity.*—An average of 3 main branches and 10 secondary branches per plant.

*Branch surface.*—Slightly glossy and smooth, bark is smooth.

*Branch aspect.*—Held at an average angle of 55°.

*Branch habit.*—Moderately to freely branching.

*Branch strength.*—Moderately strong.

*Internode length.*—An average of 9.7 cm.

*Lenticels.*—Stems densely covered with lenticels, elliptic in shape, an average of 0.5 mm in length and 0.3 mm in diameter, 161D in color.

Foliage description:

*Leaf quantity.*—An average of 8 (4 pairs) per lateral branch.

*Leaflet quantity.*—An average of 21 leaflets per leaf.

*Leaf attachment.*—Petiolate.

*Leaf arrangement.*—Opposite.

*Leaf size.*—An average of 21.8 cm in length (including petiole) and 14.1 cm in width.

*Leaflet size.*—Up to 5.8 cm in length and 3 cm in width.

*Leaflet shape.*—Ovate.

*Leaflet base.*—Attenuate.

*Leaflet apex.*—Narrowly acute.

*Leaflet venation.*—Pinnate, upper surface color; 146C to 146D, lower surface color; 146C.

*Leaflet margin.*—Incised to deeply serrate.

*Leaflet surface.*—Upper and lower surfaces matte and densely covered with soft hairs an average of 0.8 mm in length and NN155D in color.

*Leaflet color.*—Young upper surface; 137C, young lower surface; 138A and 138B, mature upper surface; 144B to 144C, mature lower surface; 144B.

*Petioles.*—About 7.2 cm in length and 0.4 mm in diameter, 143A in color, rounded in shape, moderately strong, surface is sparsely covered with strigose hairs an average of 0.5 mm in length and NN155D in color.

Flower description: No flowers have been observed to date.

It is claimed:

1. A new and distinct cultivar of *Sambucus* plant named 'Jdeboer001' substantially as herein illustrated and described.

* * * * *